(12) United States Patent
Elghazzawi et al.

(10) Patent No.: US 12,076,573 B2
(45) Date of Patent: Sep. 3, 2024

(54) MEDICAL DEVICE CONFIGURATION MANAGEMENT

(71) Applicant: ZOLL Medical Corporation, Chelmsford, MA (US)

(72) Inventors: Ziad F Elghazzawi, Newton, MA (US); Ian B Durrant, Arlington, MA (US); Henry Clay Constantine, III, Rochester, NY (US)

(*) Notice: Subject to any disclaimer, the term of this patent is extended or adjusted under 35 U.S.C. 154(b) by 216 days.

(21) Appl. No.: 17/651,149

(22) Filed: Feb. 15, 2022

(65) Prior Publication Data
US 2022/0339453 A1 Oct. 27, 2022

Related U.S. Application Data

(63) Continuation of application No. 16/211,266, filed on Dec. 6, 2018, now Pat. No. 11,285,333, which is a continuation of application No. 15/587,435, filed on May 5, 2017, now Pat. No. 10,179,245, which is a continuation of application No. 14/809,378, filed on Jul. 27, 2015, now abandoned, which is a continuation of application No. 13/558,697, filed on Jul. 26, 2012, now Pat. No. 9,119,971.

(51) Int. Cl.
*A61N 1/39* (2006.01)

(52) U.S. Cl.
CPC ......... *A61N 1/3925* (2013.01); *A61N 1/3993* (2013.01); *A61N 1/3904* (2017.08)

(58) Field of Classification Search
CPC ... A61N 1/3925; A61N 1/3993; A61N 1/3904
See application file for complete search history.

(56) References Cited

U.S. PATENT DOCUMENTS

| | | | |
|---|---|---|---|
| 6,083,248 A | 7/2000 | Thompson | |
| 6,088,616 A | 7/2000 | Olson et al. | |
| 6,356,785 B1 | 3/2002 | Snyder et al. | |
| 6,370,428 B1 * | 4/2002 | Snyder ............... | A61N 1/3904 607/5 |

(Continued)

FOREIGN PATENT DOCUMENTS

| | | |
|---|---|---|
| WO | WO2007058835 A2 | 5/2007 |
| WO | WO2007089225 A1 | 8/2007 |
| WO | WO2009136259 A2 | 11/2009 |

*Primary Examiner* — Eugene T Wu
(74) *Attorney, Agent, or Firm* — Finch & Maloney PLLC

(57) ABSTRACT

A medical device management system includes a plurality of medical devices associated with a common administrator and comprising at least one defibrillator/monitor, wherein the plurality of medical devices comprise previously stored configuration information and a central server comprising a configuration information database and configured to communicatively couple to the plurality of medical devices via a long-range wireless connection, push administrator-selected configuration information updates to the plurality of medical devices associated with the common administrator, wherein the plurality of medical devices are configured to communicatively couple with the central server via the long-range wireless connection, receive the pushed administrator-selected configuration information, and update the previously stored configuration information according to the pushed administrator-selected configuration information.

21 Claims, 6 Drawing Sheets

(56) References Cited

U.S. PATENT DOCUMENTS

| | | |
|---|---|---|
| 6,397,104 B1 | 5/2002 | Miller et al. |
| 6,398,744 B2 | 6/2002 | Bystrom et al. |
| 6,492,581 B1 | 12/2002 | Bradbury |
| 6,747,556 B2 | 6/2004 | Medema et al. |
| 6,754,526 B2 | 6/2004 | Daynes et al. |
| 6,813,517 B2 | 11/2004 | Daynes et al. |
| 6,937,150 B2 | 8/2005 | Medema et al. |
| 7,672,720 B2 | 3/2010 | Heath |
| 7,723,310 B2 | 5/2010 | Kerrish et al. |
| 7,769,465 B2 | 8/2010 | Matos |
| 7,805,190 B2 | 9/2010 | Chapman et al. |
| 7,810,723 B2 | 10/2010 | Boardman et al. |
| 7,937,146 B2 | 5/2011 | Banville et al. |
| 7,979,378 B2 | 7/2011 | West et al. |
| 8,081,071 B1 | 12/2011 | Vaisnys et al. |
| 8,214,043 B2 | 7/2012 | Matos |
| 8,781,577 B2 | 7/2014 | Freeman |
| 8,880,166 B2 | 11/2014 | Tan et al. |
| 9,119,971 B2 | 9/2015 | Elghazzawi |
| 9,364,625 B2 | 6/2016 | Silver et al. |
| 2003/0028219 A1 | 2/2003 | Powers et al. |
| 2003/0212311 A1* | 11/2003 | Nova ............ A61N 1/37258 600/300 |
| 2003/0212438 A1 | 11/2003 | Nova et al. |
| 2004/0064342 A1 | 4/2004 | Browne et al. |
| 2004/0214148 A1* | 10/2004 | Salvino ............ G16H 40/63 600/300 |
| 2005/0015115 A1 | 1/2005 | Sullivan et al. |
| 2005/0085799 A1 | 4/2005 | Luria et al. |
| 2006/0030891 A1 | 2/2006 | Saltzstein et al. |
| 2006/0084043 A1 | 4/2006 | Weaver et al. |
| 2006/0149321 A1 | 7/2006 | Merry et al. |
| 2007/0032830 A1 | 2/2007 | Bowers |
| 2007/0108274 A1 | 5/2007 | Boardman et al. |
| 2008/0138778 A1 | 6/2008 | Eggert et al. |
| 2009/0222539 A1 | 9/2009 | Lewis et al. |
| 2010/0234908 A1 | 9/2010 | Didon |
| 2010/0250643 A1 | 9/2010 | Savage et al. |
| 2011/0057082 A1 | 3/2011 | West |
| 2012/0081230 A1 | 4/2012 | Sullivan et al. |
| 2013/0012151 A1 | 1/2013 | Hankins |
| 2014/0025129 A1 | 1/2014 | Abbenhouse et al. |

\* cited by examiner

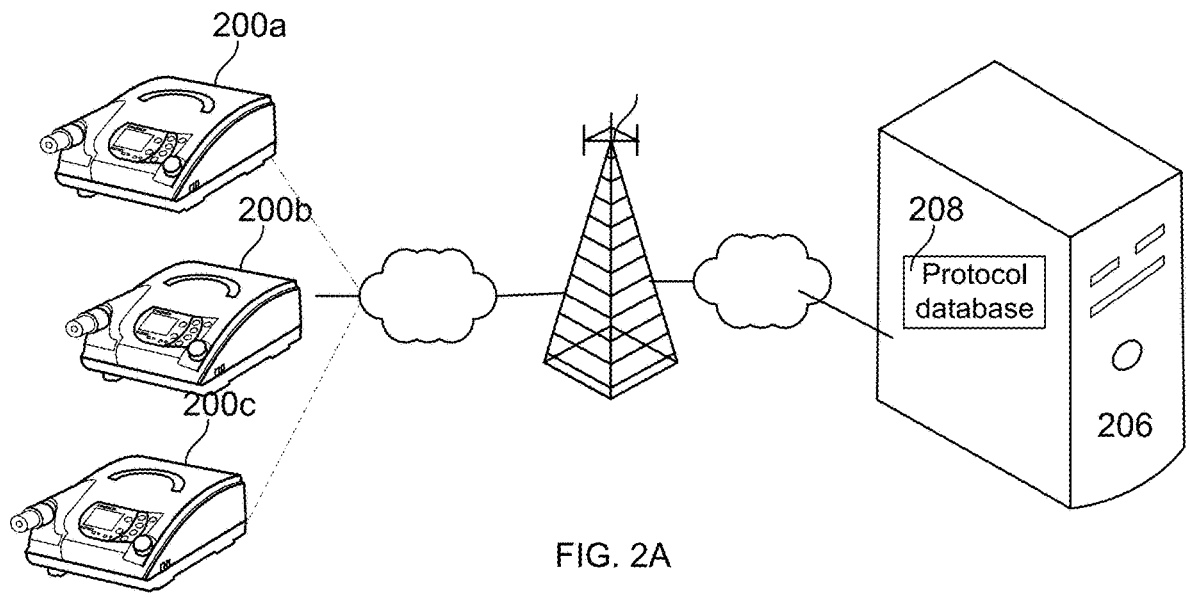
FIG. 2A
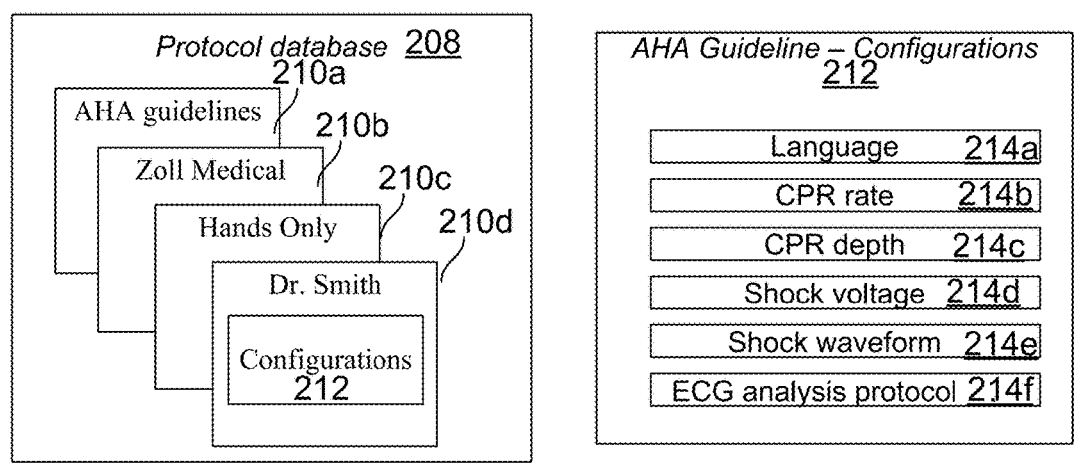
FIG. 2B
FIG. 2C

MEDICAL DEVICE CONFIGURATION MANAGEMENT

CROSS-REFERENCE TO RELATED APPLICATIONS

This application is a continuation under 35 USC § 120 to U.S. patent application Ser. No. 16/211,266, filed on Dec. 6, 2018, which is a continuation of U.S. patent application Ser. No. 15/587,435, filed on May 5, 2017 and issued as U.S. Pat. No. 10,179,245, which is a continuation of U.S. patent application Ser. No. 14/809,378, filed on Jul. 27, 2015, which is a continuation of U.S. patent application Ser. No. 13/558,697, filed on Jul. 26, 2012 and issued as U.S. Pat. No. 9,119,971. All subject matter set forth in the above referenced applications is hereby incorporated by reference in its entirety into the present application as if fully set forth herein.

TECHNICAL FIELD

This document relates to systems and techniques for configuring an Automated External Defibrillator (AED).

BACKGROUND

Sudden cardiac arrest (colloquially "heart attack") is a regular killer. The best treatment for cardiac arrest is quick and competent chest compressions to keep blood flowing through a subject's heart. Generally, every minute of delay in treating a cardiac arrest subject lowers the chance of survival by about ten percent. As a result, the ability to provide CPR in a competent manner can be a very important personal skill, and is particularly important for professional healthcare workers such as emergency medical technicians (EMTs).

Various CPR feedback devices are available that indicate to a rescuer whether they are performing CPR chest compressions at an appropriate rate and an appropriate depth of compression, such as dictated by American Heart Association (AHA) guidelines.

SUMMARY

In an embodiment, a method for configuring an automated external defibrillator includes sending, to a remote database that includes records associated with automated external defibrillator protocols used to configure automated external defibrillators, a request for available protocols for configuring the automated external defibrillator. The method also includes receiving information about one or more available protocols and sending, to the remote database, a request to download a particular one of the available protocols. The method also includes receiving, from the remote database, configuration information to automatically configure the automated external defibrillator based on the selected protocol.

In an embodiment, a method includes receiving configuration information associated with an automated external defibrillator protocol from a first automated external defibrillator and storing the protocol and the associated configuration information in an automated external defibrillator protocol database. The method also includes downloading the protocol and configuration information to a second automated external defibrillator that is different from the first automated external defibrillator.

In an embodiment, a system includes a protocol database stored in a memory, the protocol database including multiple protocol records each of which includes multiple configurations for an automated external defibrillator. The system also includes a computing device configured to receive configuration information associated with an automated external defibrillator protocol from a first automated external defibrillator, store the protocol and the associated configuration information in the protocol database, and download the protocol to a second automated external defibrillator that is different from the first automated external defibrillator.

In an embodiment, a defibrillator includes a memory configured to store a protocol comprising multiple configurations. The defibrillator also includes a computing device configured to send, to a remote database that includes records associated with automated external defibrillator protocols, a request for available protocols for configuring the automated external defibrillator, receive information about one or more available protocols, send, to the remote database, a request to download a particular one of the available protocols, receive from the remote database, configuration information to automatically configure the automated external defibrillator based on the selected protocol, store the received protocol in the memory, and configure the automated external defibrillator to operate according to the protocol stored in the memory.

The details of one or more embodiments are set forth in the accompanying drawings and the description below. Other features and advantages will be apparent from the description and drawings, and from the claims.

DESCRIPTION OF DRAWINGS

FIG. 2A shows a system for configuring an AED according to an example embodiment of the invention.

FIGS. 2B and 2C show exemplary database records and configuration entries, respectively.

DETAILED DESCRIPTION

Figure 1:
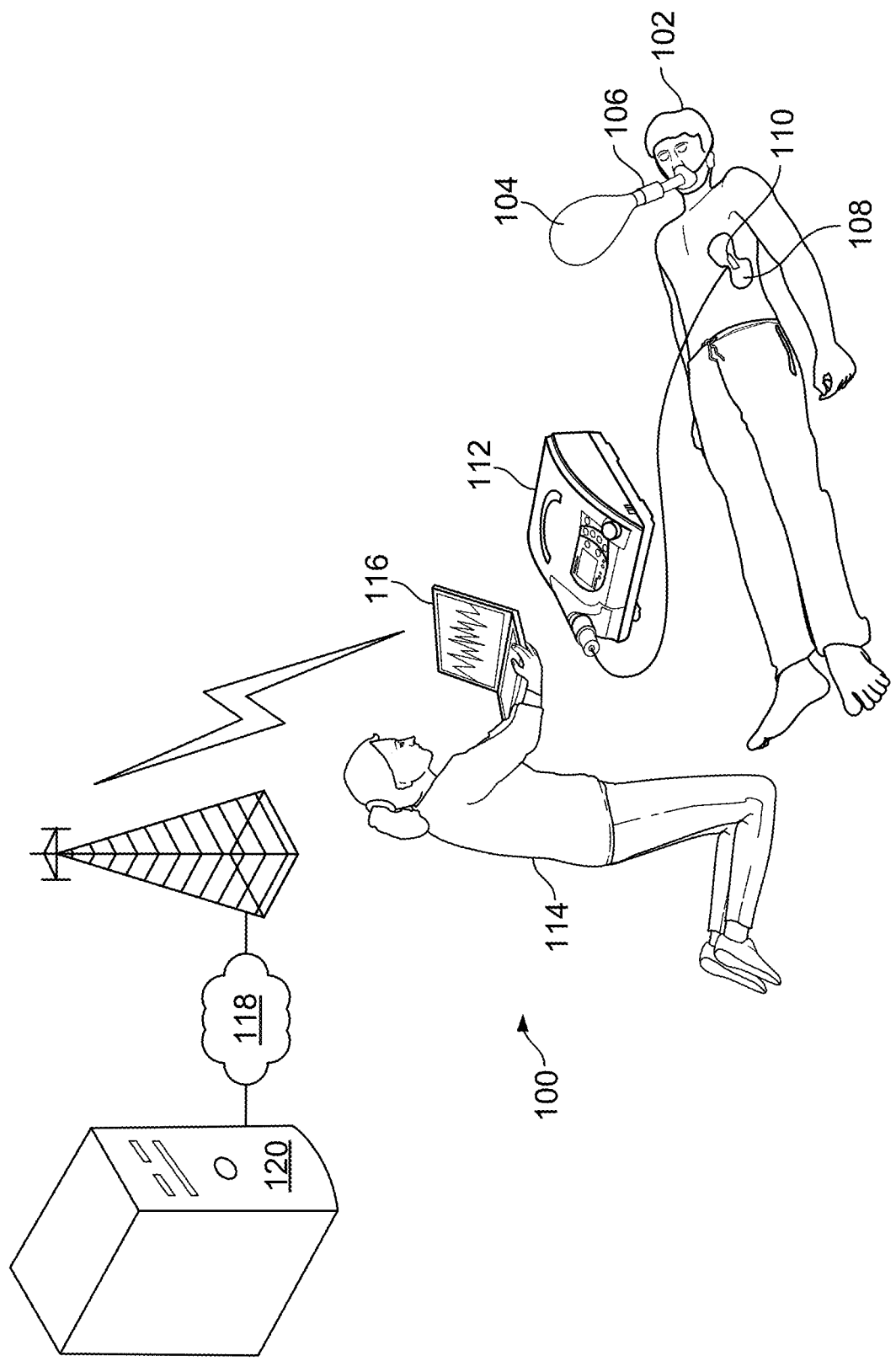
FIG. 1 shows a system for responding to an emergency medical condition according to an example embodiment of the invention.

This document describes systems and techniques that may be used to configure an AED. The AED is configured according to a protocol that outlines various configurations for the AED and causes the AED to function in a desired manner. As used herein a protocol provides guidelines on how the AED should operate and can include protocol information that provides configurations/settings for the AED such that the AED will perform and operate in a manner that conforms to the set of guidelines on how to operate the AED. For example, one portion of a protocol used by the AED can include a CPR protocol which could include protocol information and configurations to set a desired compression depth, compression rate, ventilation rate and volume, and other parameters which outline how the CPR is optimally performed. These configurations will be used to analyze CPR performance and provide feedback to the user. A protocol for the AED could additionally include guidelines regarding when and how to administer a defibrillation shock. For example, the protocol could include algorithms used in analyzing data collected from a subject such as ECG waveforms or other monitored physical parameters, shock voltages, waveforms for the defibrillation energy, timing for defibrillation, and the like. Many of the features of the protocol are stored as configurations on an AED. For example, a protocol could outline a shock voltage and this shock voltage could be stored as a configuration on the AED. Other configurations which are associated with a protocol can include configurations for the AED which do not directly relate to treatment guidelines on which the protocol is based. For example, the language in which prompts are provided to the user is not treatment guideline specific but is still a configuration stored on the AED. Protocol information, including stored AED configurations, is provided in a centrally accessible database. AED owners or administrators can store protocols in the database (e.g., by uploading the configurations from a manually configured AED and/or uploading a file with the configurations), and other AED owners or administrators can download the protocols to configure different AEDs. Thus, AED owners can share protocols and their associated configurations with one another.

In certain implementations, the systems and techniques discussed here may provide one or more advantages. For example, by providing an AED owner with a set of available protocols (which include the configurations for operation of the AED), the AED owner is able to select appropriate settings without requiring the owner to manually program the AED. Additionally, once an AED owner selects a particular protocol and downloads the protocol to the AED, updates to the configurations of the AED based on changes to the treatment guidelines on which the protocol is based can be pushed (e.g., automatically sent) to the AED. For example, when the selected protocol is modified, the modifications can be pushed to the AED. As such, the AED owner does not have to keep track of advances in treatment but rather any changes to the treatment guidelines on which the protocol is based can be automatically sent to the AED to update the AED's configurations.

This detailed description discusses examples of configuring an AED, according to at least one protocol. Protocol information, including stored AED configurations, is provided in a centrally accessible database. AED owners can store protocols in the database (e.g., by uploading the configurations from a manually configured AED and/or uploading a file with the configurations), and other AED owners can download the protocols to configure different AEDs. Thus, AED owners can share protocols and their associated configurations with one another.

For example, if a company owns five AEDs and want each of the AEDs to function in the same manner, and owner of the five AEDs can configure a first one of the AEDs manually to form a protocol for operation of the AED. The owner can then upload the newly formed protocol, including the manual configurations, as a new protocol which is stored in the central database. Because the protocol is then centrally accessible, the owner can download the protocol on to the remaining AEDs, such that the AEDs all operate using the same protocol.

FIG. 1 shows a system 100 for responding to an emergency medical condition of a subject 102. In general, system 100 includes various portable devices for monitoring on-site care given to a subject 102 of an emergency situation. The rescuer 114 in this example is interacting with a computing device in the form of a laptop computer 116 that includes a graphical display by which to report information to the rescuer 114, and may have an input mechanism such as a keyboard or a touchscreen by which the rescuer 114 may enter data into the system 100. The laptop computer 116 may also include a wireless transceiver for communicating with a wireless network, such as a 3G or 4G chipset that permits long distance communication over cellular data networks, and further through the internet.

Separately, a portable defibrillator 112 is shown in a deployed state and is connected to the subject 102. In addition to providing defibrillation, the defibrillator 112 may serve as a subject monitor via a variety of sensors or sensor packages. For example, as shown here, electrodes 108 connected to the defibrillator 112 have been applied to the subject 102 so that electrical shocking pulses may be provided to the electrodes in an effort to defibrillate the subject 102, and electrocardiogram (ECG) signals may be read from the subject 102. Further examples of use of the portable defibrillator are described, for example, in U.S. Ser. No. 13/398,280 filed on Feb. 16, 2012 and entitled "Coordinated Resuscitation Perfusion Support", the contents of which are hereby incorporated by reference. The defibrillator operates according to a protocol that includes set of configurations stored on the defibrillator.

The defibrillator 112 may include an accelerometer assembly 110 configured to identify a vertical displacement caused by CPR compressions (e.g., to compute the displacement of the subject's breastbone for comparison to American Heart Association (AHA) guidelines). In response to receiving such information from the accelerometer assembly 112, the defibrillator 112 can provide feedback to a rescuer, for example, the defibrillator 112 may generate a metronome to pace such a user in providing chest compressions. In addition, or alternatively, the defibrillator 112 may provide verbal instructions to the rescuer, such as by telling the rescuer that they are providing compressions too quickly or too slowly, or are pushing too hard or too soft, so as to encourage the rescuer to change their technique to bring it more in line with proper treatment guidelines—where the proper treatment guidelines may be any protocol stored on the AED and need not be a protocol based on standard, published treatment guidelines. In addition, similar feedback may be provided visually on a screen of the defibrillator, such as by showing a bar graph or number that indicates depth and another that indicates rate, with appropriate mechanisms to indicate whether the depth and rate or adequate, too low, or too high. Examples of such feedback are described, for example, in U.S. Ser. No. 13/025,348, filed on Feb. 11, 2011 and entitled "Defibrillator Display", the contents of which are hereby incorporated by reference.

The defibrillator can additionally be provided with a ventilation bag 104 that includes an airflow sensor 106. The airflow sensor 106 may be configured to monitor the flow of air into and out of the subject's mouth, so as to identify a rate at which ventilation is occurring with the victim. In addition, in certain implementations, the airflow sensor 106 may be configured to monitor a volume of airflow into and out of the subject 102. This information can be used to provide feedback to the rescuer about ventilation, for example, as described in U.S. Ser. No. 13/081,217 filed on Apr. 6, 2011 and entitled "Wireless Ventilation Reporting", the contents of which are hereby incorporated by reference. The feedback provided to the rescuer is based on the protocol stored on the defibrillator.

The defibrillator 112 may communicate through a short range wireless data connection with the laptop computer 116 to provide to the laptop computer 116 status information, such as information received through the electrode assembly 108, including ECG information for the subject 102. Also, the defibrillator 112 can send information about the performance of chest compressions, such as depth and rate information for the chest compressions.

Where described herein, the processing and display of data may occur on the defibrillator 112, the laptop computer 116, or on both. For example, the defibrillator 112 may include a display that matches that of the laptop computer 116, and the two may thus show matching data. In contrast, the defibrillator 112 may have a more limited display than does the laptop computer 116, and might show only basic information about the technician's performance, while the laptop computer 116 may show more complete information such as secondary historic information. Also, the processing of primary information to obtain secondary information may be performed by the defibrillator 112, the laptop computer 116, or a combination of the two, and the two devices may communicate back and forth in various manners to provide to each other information they have received or processed, or to relay commands provided to them by the rescuer 114.

A central server system 120 may communicate with the laptop computer 116, the defibrillator 112, or other devices at the rescue scene over a wireless network and a network 118, which may include portions of the Internet (where data may be appropriately encrypted to protect privacy).

The defibrillator 112 and associated devices can function based on a protocol stored on the system. The configurations included in the protocol can be based on treatment guidelines, for example, based on the American Heart Association Guidelines for Cardiopulmonary Resuscitation (AHA CPR). The defibrillator can initially be installed to operate based on a standard protocol such as the AHA protocol, however, a user or owner of the defibrillator could override the initial configurations to have the device operate using a different protocol or to update the device as the protocols change. In some examples, the new or updated protocol could be downloaded from a central computer server to the defibrillation device. Such an approach may have the benefit of being able to easily update and modify settings/configurations of the AED to implement the desired protocol.

The computing device may then receive information about the performance by the rescuers, such as from wired or wireless transmitters on a defibrillator, an assisted ventilation unit, or other medical device (e.g., blood pressure reader). The computing device may provide feedback or coaching when the performance falls out of line with a defined protocol stored on the AED, or may provide feedback to maintain the performance in line with the protocol. In providing the feedback, the computing device or the defibrillator may generate a number of derived parameters from measured parameters of the subject, and both the measured parameters and the more comprehensive derived parameters may be reported visually or audibly by the computing device, the defibrillator/monitor, or both.

FIG. 2A is a diagram of multiple defibrillation devices 200a, 200b, and 200c connected to a central server 206 that includes a protocol database 208. The protocol database can include information about the protocol such as the AED configurations used to operate the defibrillation devices 200a, 200b, and 200c. The database 208 provides centralized access to the multiple, different protocols (including the configuration information used to set the defibrillator configurations) by various AEDs communicatively connected to the database by a wired or wireless connection. For example, a particular one of the defibrillation devices can modify the protocol stored on the AED by requesting to download an updated or a different protocol from the protocol database 208 (e.g., the AED can download a protocol with different configuration settings that is based on the same or a different set of treatment guidelines). Additionally, protocols can be uploaded to the protocol database 208 so that the protocols will be accessible for download onto other AEDs. For example, an owner or user of the defibrillation device can manually update the protocol used to operate the AED (e.g., manually change one or more of the device configurations) and then store the configurations associated with the updated protocol in the protocol database 208. By storing the protocol including the configuration information in the protocol database 208, this set of configurations will be available to be downloaded onto another, different defibrillation device such that the same protocol (e.g., the updated protocol) can be used to operate the other defibrillation device without having to manually configure the device.

The communication between the defibrillation devices 200a, 200b, and 200c and the central server 206 can occur over a wireless network such as a cellular network. For example, the defibrillation devices 200a, 200b, and 200c can include a wireless transceiver for communicating with a wireless network, such as a 3G or 4G chipset that permits long distance communication over cellular data networks, and further through the internet. In additional examples, a tablet, laptop computer, or other computing device associated with the defibrillation device can include the wireless transceiver for communicating with the wireless network and the defibrillation device can include a short range communication chip to communicate with the tablet, laptop computer, or other computing device. In such an arrangement, the tablet, laptop computer, or other computing device communicates with both the central server 206 and with the defibrillation device.

As shown in FIG. 2B, the protocol database 208 stored in the memory associated with the central server 206 includes multiple records 210a-d each of which is associated with a particular stored protocol. Each of these records includes multiple configurations 212. These configurations are used to configure a defibrillation device. For example, as shown in FIG. 2C, each stored protocol can include settings for items such as language 214a, CPR rate 214b, CPR depth 214c, shock voltage 214d, shock wave form 214e, and ECG analysis protocol 214f.

Figure 3A:
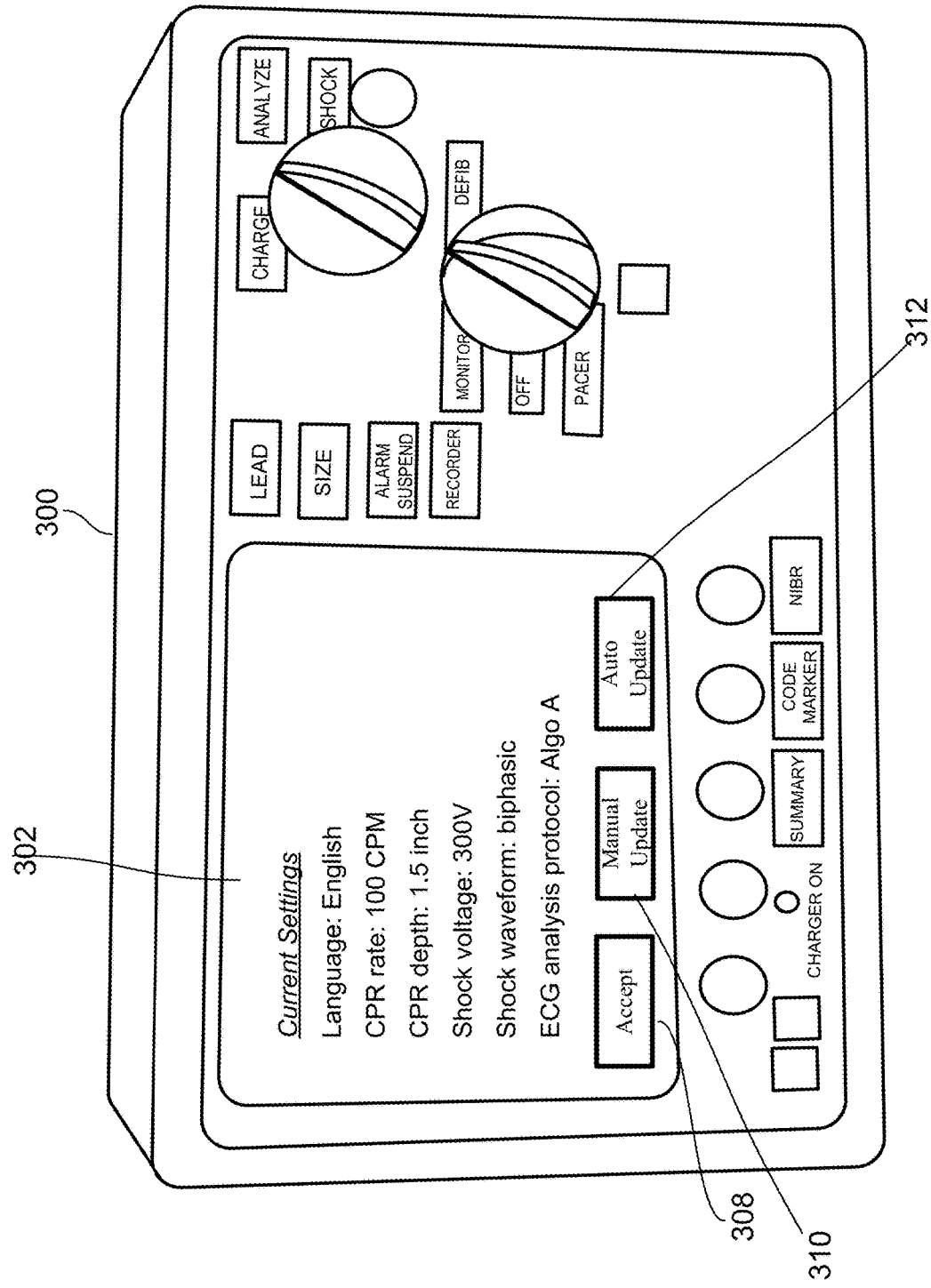
FIG. 3A shows an AED including a display screen according to an example embodiment of the invention.

FIG. 3A shows an exemplary defibrillation device 300 that includes a display 302 showing the current settings for the defibrillation device. During use, or during an initial setup, a user may desire to change the configurations for the defibrillation device. In order to modify the configurations, the user can manually update the configurations by selecting button 310, or automatically update the settings by downloading a set of configurations (e.g., a different protocol) from the central database by selecting button 312. When the user is satisfied with the configuration, the user can accept the configurations by selecting button 308.

Figure 3B:
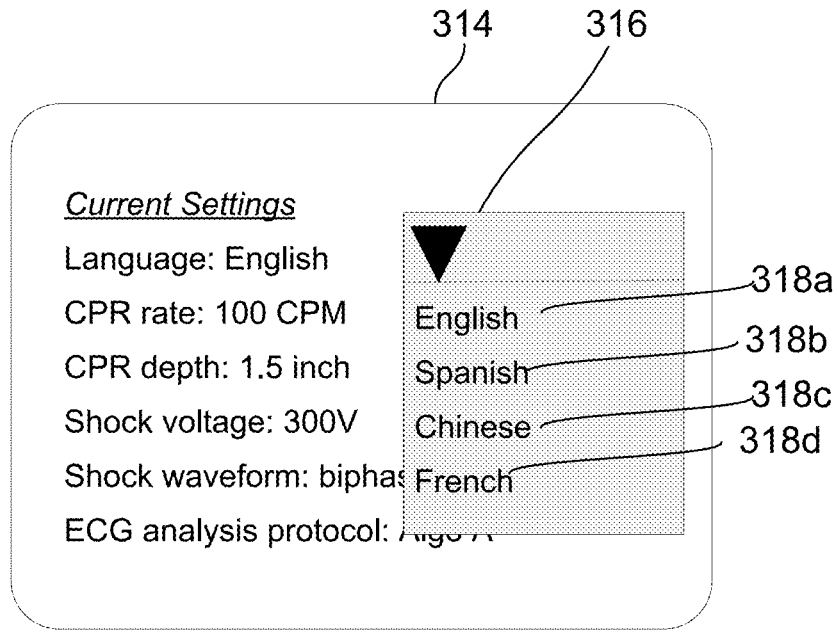
FIGS. 3B and 3C are screen shots of AED configuration screens according to an example embodiment of the invention.

If the user selects to manually update the configurations (e.g., by selecting the manual update option by pressing button 310), the defibrillation device displays the current configurations and options for amending those configurations. For example, FIG. 3B, shows an exemplary user interface for manually modifying the configurations of the defibrillation device. By selecting a drop-down menu associated with a particular configuration, the user can modify the configuration. In the exemplary display of FIG. 3B, the user has selected to modify the language used on the display and for the audio prompts. In order to change the language from the currently selected language of English, the user selects the drop-down menu 316 and then clicks on a particular one of the available languages 318a-d. Thus, the user can modify the configurations used by the defibrillator by manually changing one or more of the configurations. The amended configurations can form a new or updated protocol that includes any changes to the configurations of the original protocol. The new or updated protocol can be stored on the defibrillation device and optionally uploaded to the central database 208.

Figure 3C:
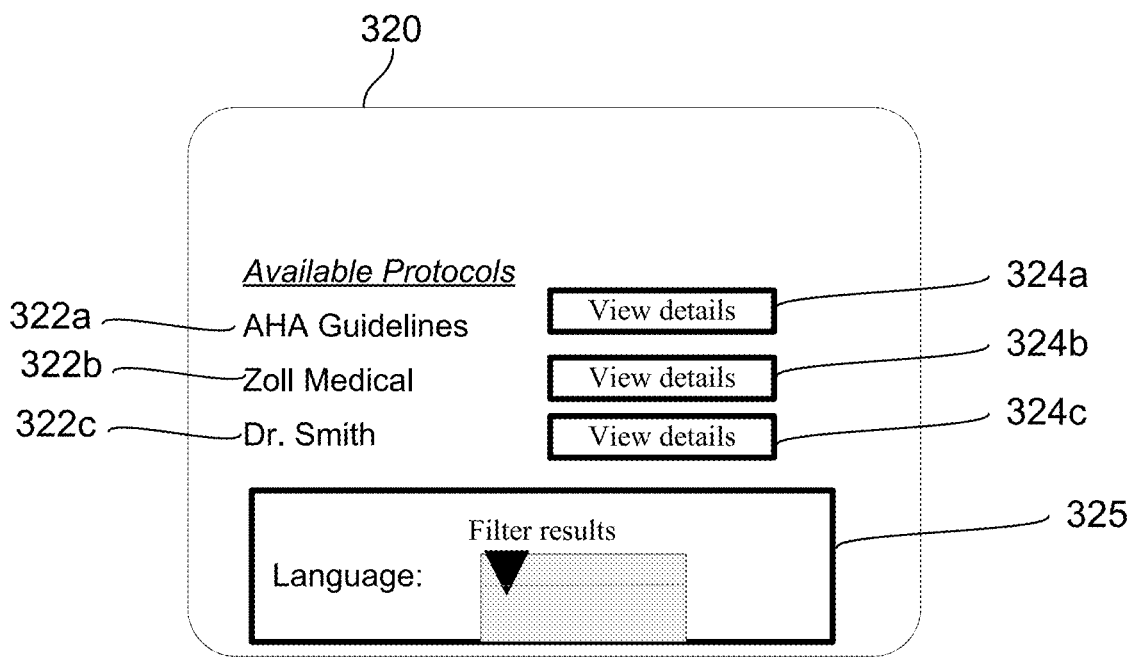

If the user selects to automatically update the configurations (e.g., by selecting the automatic update option by pressing button 312), the defibrillation device displays a listing of available protocols as shown in the user interface 320 shown in FIG. 3C. The user interface 320 displays a list of available protocols (e.g., protocols 322a-c). A user can select to see additional details about a particular protocol by selecting the associated view details button (e.g., buttons 324a-c). For example, to view the details (e.g., the particular configuration settings) of the AHA guideline protocol 322a the user would select view details button 324a.

The list of protocols that are available can be filtered to assist a user in identifying a particular protocol. In some examples, the set of protocols is automatically filtered based on the model of the AED. And some additional examples, a user can filter the list of available protocols to narrow the number of protocols to select from based on one or more features of interest to the user. For example, key features of protocols (such as key configurations) can be displayed and the user can select from drop-down menus to filter the available protocols based on the setting for a particular configuration. For example, as shown in FIG. 3C, the user can select to filter the results based on the language (e.g., using the drop down menu in filter box 325) such that only protocols in the selected language will be displayed. Other key features, such as whether the CPR protocol relies on hands only CPR, the CPR rate, the analysis protocols, or the shock voltage could be used to filter the results. In some examples, the results could be filtered based on multiple, different features.

In some examples, protocols stored in the protocol database can have associated skill level indicators and the list of available protocols can be filtered based on an anticipated skill level of the rescuer. In some additional examples, a combination of language and skill level can be used to filter the list of available protocols.

Figure 4A:
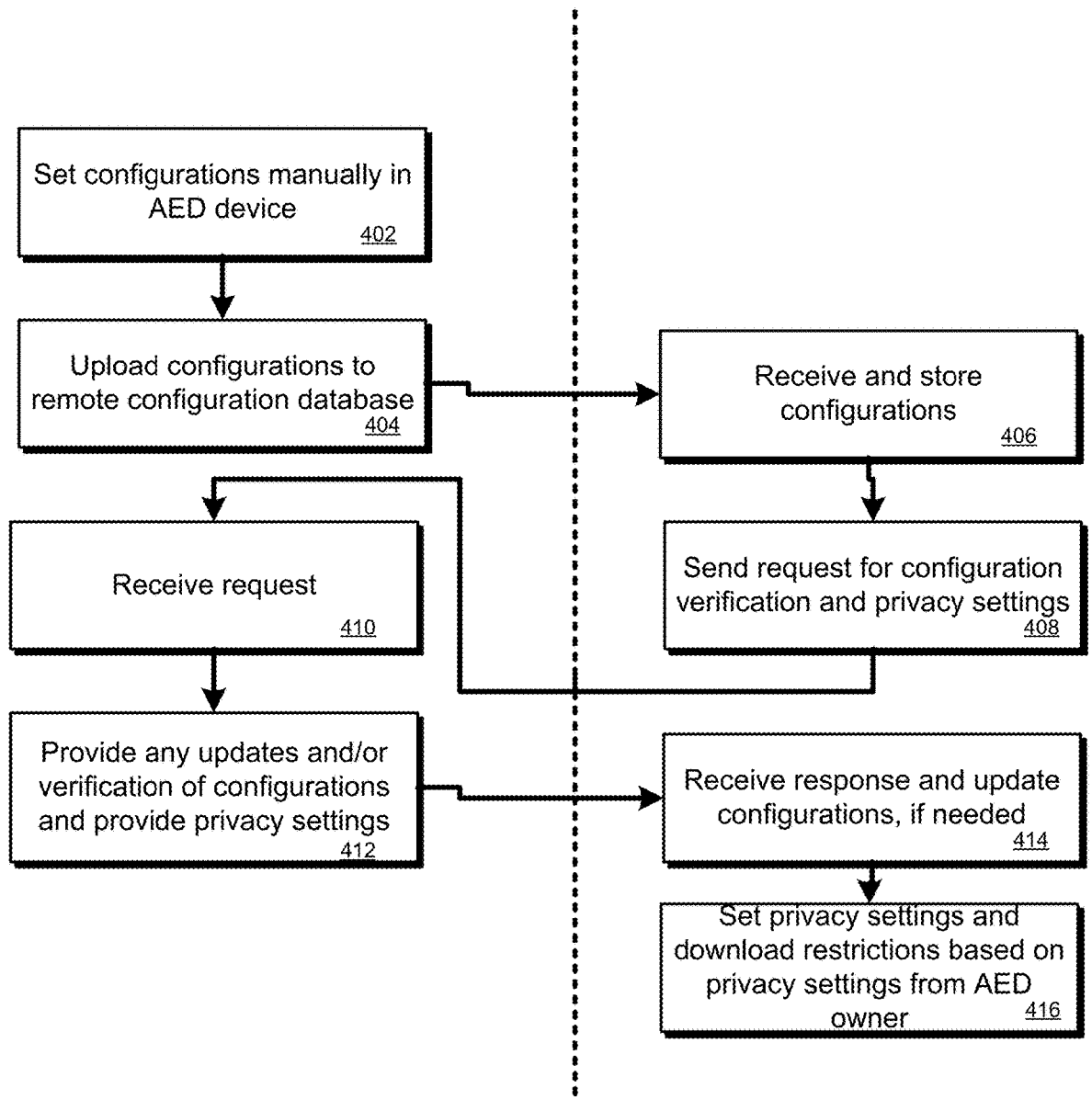
FIG. 4A is a multi-entity flow diagram of a process for uploading and storing AED protocols according to an example embodiment of the invention.

FIG. 4A shows a multi-entity flow diagram of a process for storing AED protocols in a centralized database. The process begins with a user setting the configurations of an AED manually (402). For example, the user can progress through a set of predefined screens to select different configurations. Values for these configurations can be based on existing protocols or can be set to a desired set of configurations that is different from the configurations of an existing protocol. After manual configuration of the AED is complete, the user uploads the protocol, including all of the associated configurations to a remote configuration database (404). For example, the user can select an 'upload configuration' or 'export configuration' option and the configurations for the new protocol can be wirelessly uploaded to the remote database using a cellular connection.

The remote server receives the protocol information, including the configurations from the AED and stores the protocol information in the protocol database as a new entry (406). The user can select a name or identifier to associate with the uploaded protocol. Associating a user-selected name can enable the user or another user to later locate the protocol and download the protocol to additional AEDs.

After storing the configurations for the uploaded protocol, the central server sends a request for verification of the configurations for the protocol and a request for information about privacy settings to associate with the protocol (408). The AED receives the request (410), and provides any user-input updates and/or verification of the configurations and the requested privacy settings to the central server (412). The central server receives the user input response and, if needed, updates the stored configurations for the protocol (414). The central server also sets the privacy settings for the protocol (including any downloading restrictions) based on the privacy settings from the AED owner (416). For example, and AED owner may restrict download of their protocols to others within the same Corporation, others having the same hospital affiliation, other AEDs maintained by the same AED servicing group, etc.

Figure 4B:
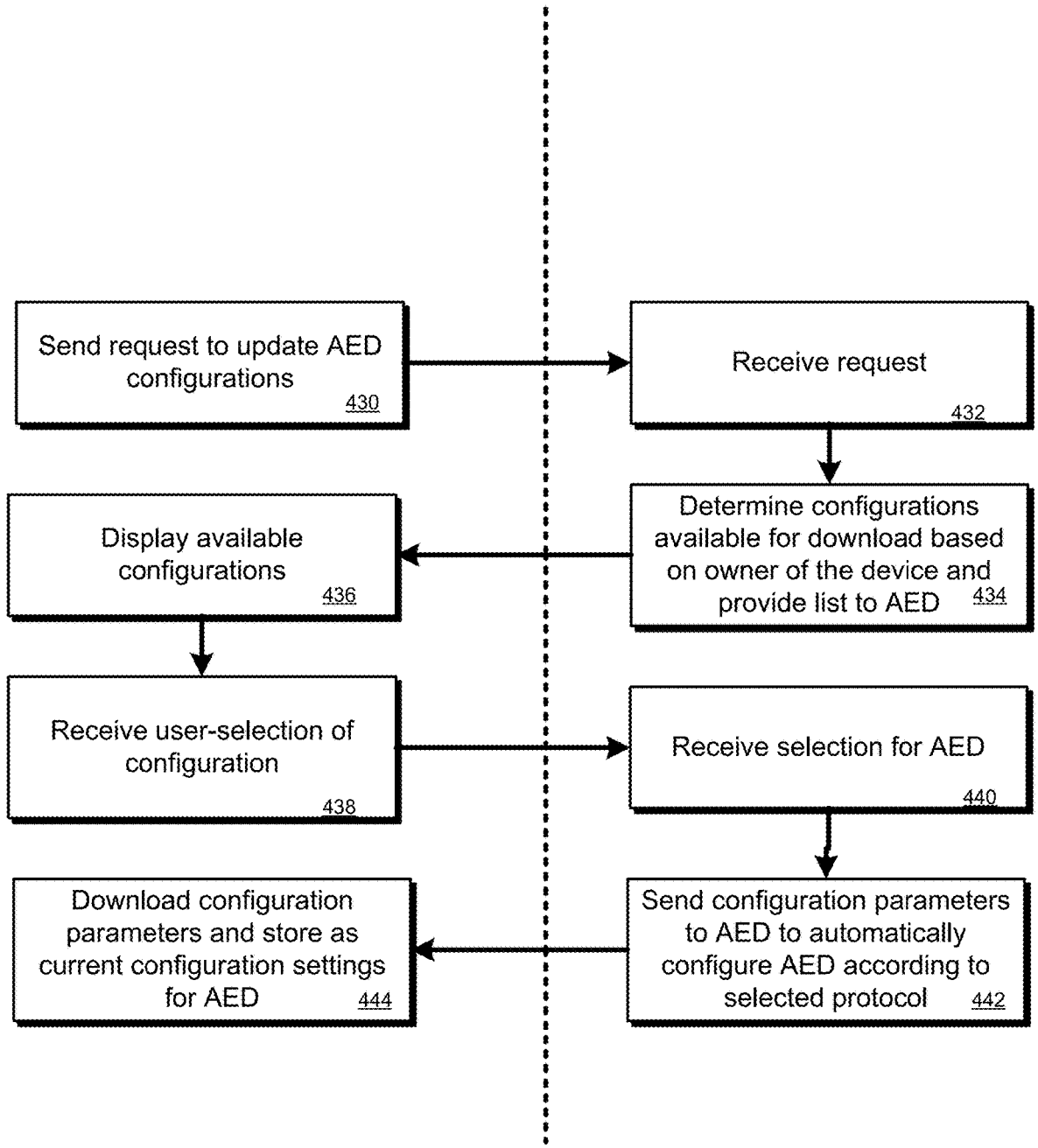
FIG. 4B is a multi-entity flow diagram of a process for downloading AED protocols according to an example embodiment of the invention.

FIG. 4B is a multi-entity flow diagram of a process for downloading a protocol to an AED and configuring the AED based on the configurations stored in the protocol. The process begins with an AED sending a request to update/change the protocol for the AED (430). The central server that includes a protocol database receives the request (432) and determines protocols that are available for the user to download based on ownership and/or a model of the AED (434). The central server provides a list of the available protocols to the AED and the list of available protocols is displayed on the AED, or an associated device (436). The AED receives a user selection of one of the protocols from the list of protocols (438). This selection is sent to the central database and the central database receives an indication of the selected protocol (440). The central database then sends configurations associated with the protocol to the AED which will automatically configure the AED according to the selected protocol (442). The AED downloads the protocol, including the configurations, and stores the received configurations as the current settings for the AED (444). Thus, a user is able to select a protocol from a list of protocols and have the settings for the AED automatically configured according to the configurations in the protocol by downloading the desired protocol.

In some embodiments, updates to a protocol (e.g., changes to one or more configurations of the protocol) can be automatically pushed to AEDs operating based on the protocol. For example, if an owner of an AED downloads the AHA protocol and the AHA protocol is later updated (e.g., one or more of the configurations is changed) then the updates to the configurations can be automatically sent to the AED. As such, the initial protocol is downloaded by the user (e.g., pulled from the database at the central server) and the updates are automatically sent (e.g., pushed to the AED from the central server) to the AED.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A medical device management system comprising:
   a plurality of medical devices associated with a common administrator and comprising at least one defibrillator/monitor, wherein the plurality of medical devices comprise previously stored configuration information; and
   a central server comprising a configuration information database and configured to:
      communicatively couple to the plurality of medical devices via a long-range wireless connection,
      push administrator-selected configuration information updates to the plurality of medical devices associated with the common administrator,
   wherein the plurality of medical devices are configured to:
      communicatively couple with the central server via the long-range wireless connection,
      receive the pushed administrator-selected configuration information, and
      update the previously stored configuration information according to the pushed administrator-selected configuration information.

2. The system of claim 1, wherein the plurality of medical devices associated with the common administrator have a same hospital affiliation.

3. The system of claim 2, wherein the plurality of medical devices associated with the common administrator are configured for use in intensive care unit patient monitoring.

4. The system of claim 1, wherein the central server includes model information for the plurality of medical devices.

5. The system of claim 1,
   wherein the at least one defibrillator/monitor is communicatively coupled to a respective computing device via a short-range wireless connection, and
   wherein the respective computing device displays data that matches data provided at a display of the at least one defibrillator/monitor.

6. The system of claim 5, wherein the respective computing device comprises a touchscreen configured to report information to a rescuer.

7. The system of claim 6, wherein the information reported at the touchscreen comprises information received through an electrode assembly coupled to the at least one defibrillator/monitor.

8. The system of claim 7, wherein the information received through the electrode assembly comprises electrocardiogram (ECG) information.

9. The system of claim 7, wherein the information reported at the touchscreen comprises data that matches the display of the at least one defibrillator/monitor and additional information absent from the display of the at least one defibrillator/monitor.

10. The system of claim 9, wherein the additional information absent from the display of the at least one defibrillator/monitor comprises historic information.

11. The system of claim 9, wherein the display of the at least one defibrillator/monitor is configured to provide visual cardiopulmonary resuscitation (CPR) compression feedback.

12. The system of claim 11, wherein the CPR compression feedback comprises a bar graph or number that indicates compression depth, a bar graph or number that indicates compression rate, and an indication of whether the compression depth and the compression rate are adequate, too low, or too high.

13. The system of claim 6, wherein the at least one defibrillator/monitor is configured to couple to an airflow sensor.

14. The system of claim 13, wherein the information reported to the rescuer comprises ventilation feedback.

15. The system of claim 5, wherein the respective computing device comprises a tablet computer.

16. The system of claim 5, wherein the central server is communicatively coupled to the respective computing device by the long-range wireless connection.

17. The system of claim 1, wherein the pushed administrator-selected configuration information is the same for all of the plurality of medical devices associated with the common administrator.

18. The system of claim 1, wherein the pushed administrator-selected configuration information comprises settings for one or more of cardiopulmonary resuscitation (CPR), shock voltage, shock waveform, or language.

19. The system of claim 1, wherein the pushed administrator-selected configuration information comprises settings for electrocardiogram (ECG) analysis.

20. The system of claim 1, wherein the long-range wireless connection comprises one or more of a wireless cellular connection or a wireless computer network connection.

21. The system of claim 1, wherein the pushed administrator-selected configuration information comprises configuration updates.

* * * * *